United States Patent [19]

Bernardi et al.

[11] Patent Number: 4,843,146

[45] Date of Patent: Jun. 27, 1989

[54] IMMUNOLOGICALLY ACTIVE POLYPEPTIDES USEFUL FOR THE PREPARATION OF ANTIMALARIAL VACCINES AND OF DIAGNOSTIC KITS FOR THE DETECTION OF ANTISPOROZOITE ANTIBODIES

[75] Inventors: Adriano Bernardi, Monterotondo; Fabio Bonelli; Antonello Pessi, both of Rome; Antonio S. Verdini, Monterotondo, all of Italy

[73] Assignee: Eniricerche, S.p.A., Milan, Italy

[21] Appl. No.: 128,082

[22] Filed: Dec. 3, 1987

[30] Foreign Application Priority Data

Dec. 4, 1986 [IT] Italy ............................... 22560 A/86

[51] Int. Cl.$^4$ ..................... C07C 103/52; A61K 39/00
[52] U.S. Cl. ...................................... 530/324; 424/88; 435/7
[58] Field of Search ......................... 424/88; 530/324; 514/895

[56] References Cited

PUBLICATIONS

Dame, *Science*, 225, 593 (1984).
Gibson, *Proc. Natl. Acad. Sci.*, USA, 83, 5649 (1986).
Del Giudice, *The Journal of Immunology*, 137, 2952 (1986).

*Primary Examiner*—Margaret Moskowitz
*Assistant Examiner*—F. T. Moezie
*Attorney, Agent, or Firm*—Hedman, Gibson, Costigan & Hoare

[57] ABSTRACT

Immunologically active polypeptides constituted, towards the N-terminated end, by an Asn-Val-Asp-Pro-Asn-Ala-Asn-Pro sequence repeated three times and, towards the C-terminated end, by at least three quadruplets with an Asn-Ala-Asn-Pro sequence, linked with each other by means of an amidic bond between the end proline of the first sequence, and the initial asparagine of the first quadruplet.

Said polypeptides reproduce nearly exactly the sequential structure of the circumsporozoite protein of P. falciparum, and are useful for the preparation of antimalarial vaccines and of diagnostic kits for the detection of antisporozoite antibodies in clinical samples of malariated persons.

2 Claims, No Drawings

IMMUNOLOGICALLY ACTIVE POLYPEPTIDES USEFUL FOR THE PREPARATION OF ANTIMALARIAL VACCINES AND OF DIAGNOSTIC KITS FOR THE DETECTION OF ANTISPOROZOITE ANTIBODIES

The present invention relates to immunologically active polypeptides useful for the preparation of antimalarial vaccines and of diagnostic kits for the detection of antisporozoite antibodies in clinical samples from malariated persons.

The invention relates furthermore to a method for the preparation of said polypeptides.

The etiologic agent of malaria is a protozoan parasite belonging to Plasmodium genus, having a vital cycle alternating between an invertebrate host, wherein it shows a sexual form of reproduction, and a vertebrate host, inside which it multiplies by simple schizogenesis.

Among the hundreds of species of Plasmodium existing in nature, only four are pathogen for man: *P. ovale*, *P. vivax*, *P. malariae*, and *P. falciparum*.

This latter, in particular, represents the etiological agent of the most serious form of malaria, the so-said "tertian malignant malaria".

At present, malaria represents one of the most serious parasitic diseases for man.

Said disease is estimated in fact to strike, each year, from 200 to 400 million people, causing a mortality rate during the early infancy which can be as high as 50% of cases.

The need derives from the above, of developing an efficacious antimalarial vaccine, i.e., a vaccine which is capable of stimulating the production of antibodies which are able to attack and neutralize the parasite, and develop a permanent protective immunity.

The malarial infection in man begins with the bite of the anopheles mosquito, which releases, inside the blood stream, a certain number of sporozoites.

Within one hour, each sporozoite reaches a hepatic cell wherein it will give rise to the formation of 20,000 or more merozoites.

Then, each merozoite invades an erythrocyte, wherein it multiplies asexually, from rings into schizonts.

The mature schizont contains individual merozoites, which are not yet capable of invading other erythrocytes.

When the erythrocyte explodes, it releases from 10 to 20 mature merozoites, some of which turn into gametocytes, which represent the mosquito infecting form.

The complex structure of the vital cycle of the malarian parasites has made it difficult, up to date, to develop a vaccine endowed with the desired characteristics.

These parasites develop in fact according to a multi-step cycle, exposing to the host organism a very large number of antigenic components, which are different from one another, and stage-specific.

Only a small fraction of these antigenic components induce immuno-protective responses, whilst the other fractions either are immaterial for the purpose of an immune protection, or stimulate undesired responses in the host.

The vaccination by means of the use of the whole parasite is therefore a neither valid nor practicable approach, in that the malarian parasites cannot be obtained in a large enough amount, or at a satisfactory purity level.

Therefore, the strategy for the development of an antimalarian vaccine should be based on the identification and characterization of the only parasitic antigens which specifically stimulate immuno-protective reponses.

Once that the aminoacidic sequence of the natural protein has been identified, the next step consists in preparing and active molecule, and/or active fragments thereof, by means of methods of chemical synthesis, or of genetic engineering.

During the past years, in an attempt to identify protective plasmodial antigens, the researchers focused their interest towards the extracellular forms: merozoites, sporozoites and gametocytes, the only forms which are exposed to the immunity system.

In particular, many studies were carried out about the identification and characterization of antigens bound to the sporozoite.

In fact, the development of a vaccine against this form of the parasite is particularly desired in that, if it is efficacious on man, it can inhibit the successive steps responsible for the disease and for the transmission of the infection.

Recently, it was demonstrated that the main membrane antigen of a sporozoite of *P. falciparum* is a protein, denominated "circumsporozoitic protein", or "CS", covering the whole surface of the sporozoite.

Said protein results to be constituted by 412 aminoacids with a central domain constituted by tetrapeptides with an Asn-Ala-Asn-Pro sequence repeated 37 times, and by 4 tetrapeptides with an Asn-Val-Asp-Pro sequence (Dame et al., Science, 1984 225, 593; Nussenzweig et al., Cell, 1985 42, 401).

In the technical and patent literature, processes are reported for the synthesis of proteins which contain the repeating sequences ASN-ALA-ASN-PRO both via recombinant DNA, and by chemical synthesis.

The processes which use the genetic engineering techniques show however some drawbacks, such as the use of the pathogen microorganism E. coli, and obtainment of a fused protein, i.e., a protein constituted by the CS protein and a heterologous aminoacidic sequence.

A process for the chemical synthesis is disclosed in co-pending Italian patent application No. 21718 A/85 which discloses and claims a peptidic sequence constituted by a mixture of peptides, wherein the (Asn-Ala-Asn-Pro) sequence is repeated n times.

From the studies carried out for the purpose of determining the immunological properties of said composition, and determining its capability of inducing a protective immunity, it was observed that the peptidic fraction containing an average of 40 (Asn-Ala-Asn-Pro) quadruplets, although is highly immunogen, induces a genetically restricted immune response.

In fact, only some T cellular clones, in laboratory mice, are stimulated by such fraction.

This constitutes a disadvantage for the development of an antimalarian vaccine, in that it is not efficacious on all patients.

The present Applicant found now that it is possible to overcome the drawbacks of the prior art, by means of immunologically active polypeptides, which can be obtained in a pure form by a simple and economically favourable process, and comprise, besides the Asn-Ala-Asn-Pro sequence, still other peptidic segments present in the protein of the parasite.

A purpose of the present invention is therefore immunologically active polypeptides useful for the preparation of antimalarial vaccines and of diagnostic kits for detecting antisporozoite antibodies in clinical samples.

Another purpose of the present invention is also the use of said polypeptides for preparing antimalarial vaccines and diagnostic kits for detecting antisporozoite antibodies in clinical samples.

Still another purpose of the present invention is a process for the preparation of said polypeptides.

Still further purposes of the invention will be clear from the following disclosure of the text and from the following Examples.

In particular, polypeptides according to the present invention can be defined by means of the following general formula (I):

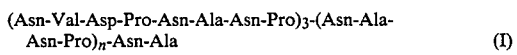
(I)

wherein:
Asp=aspartic acid
Asn=asparagine
Ala=alanine
Pro=proline
Val=valine and wherein n has a value equal to, or higher than, 3.

The polypeptide (I) can be prepared, according to known general techniques, either in homogeneous phase, or in solid phase.

According to the present invention, the polypeptide (I) is synthetized in the solid phase by means of a process comprising:

(a) the condensation of the first aminoacid (Ala) protected on the α-amino group onto an insoluble solid support by means of a reaction of esterification between the activated carboxy group and the connection hook of the solid support;

(b) the removal of the protecting group from the α-amino group;

(c) the condensation of the Ala aminoacid bonded to the insoluble solid support onto the second Asp aminoacid protected on its α-amino group by means of a reaction of acylation between the de-protected amino group and the activated carboxy group of the second aminoacid;

(d) the removal of the α-amino-protecting group from the second aminoacid;

(e) the condensation of the successive aminoacids according to the strategies as per above (c) and (d) steps, until polypeptide (I) is complete;

(f) the removal of the so-obtained polypeptide (I) from the insoluble solid support by means of an acidic hydrolysis;

(g) the recovery and purification of polypeptide (I) by chromatography.

According to the present invention, insoluble solid supports are selected from polyacrylamidic resins, polystyrene resins crosslinked with divinyl-benzene, phenolic resins.

In particular, a commercial polyacrylamidic resin, which is functionalized with norleucine (Nle) as the internal reference aminoacid, and a hook for the formation of the reversible peptide-resin link, such as, e.g., p-hydroxymethylphenoxyacetic acid, is used.

Before condensing the aminoacids, the functionalized resin is swollen by means of a treatment with N,N-dimethyl-formamide (DMF), at room temperature, or at temperatures close to room temperature.

According to the present invention, the aminoacids can be added to the resin either individually or, after a preliminary synthesis in homogeneous phase, as preconstituted peptides.

The aminoacids are condensed onto the resin after a preliminary protection of the α-amino group, and of the possible reactive functions on side chains, and the activation of the end carboxy group.

Examples of α-amino protecting groups suitable for the intended purpose are: benzyl-oxy-carbonyl, triphenyl-methyl, tert.-amyl-oxy-carbonyl, 2-nitro-phenylsulphonyl, fluorenyl-methyl-oxy-carbonyl (Fmoc) and tert.-butyl-oxy-carbonyl (Boc).

From these, the Fmoc and Boc groups, which can be removed under mild operating conditions, are preferred.

The fluorenyl-methyl-oxy-carbonyl (Fmoc) group is particularly preferred.

Possible reactive functional groups present in the side chains of the aminoacids are protected with protecting groups known in the art of peptide syntheses.

Typically, protecting groups are used, which are stable under the conditions of removal of the α-amino protecting group.

An example for said protecting groups for aspartic acid is tert.-butyl-ester (OBu$^t$).

According to the present invention, the activation of the aminoacidic radicals Val, Ala, Pro, Asp is carried out by means of the reaction with dicyclohexyl-carbodiimide (DCI), to form the symmetrical anhydride of said aminoacid at the end carboxy group.

Generally, the reaction is carried out by dissolving the aminoacid, with its α-amino group being protected, in an inert (non-reactive) organic solvent, in the presence of di-cyclo-hexyl-carbodiimide, at room temperature (20°–25° C.).

After the end of the reaction, dicyclohexylurea is filtered or centrifuged off, the solvent is evaporated off and the so-formed symmetrical anhydride is recovered.

The activation of Asn aminoacid radical is carried out by means of the reaction with a derivative of phenol, to form the active ester on the end carboxy group.

Phenol derivatives which can be used in the process according to the present invention are the fluorinated or chlorinated phenol derivatives, such as, e.g., pentachlorophenol, trichlorophenol, pentafluorophenol and p-nitrophenol.

The reaction of activation of the carboxy group of the α-amino-protected aminoacid is carried out by contacting said aminoacid and said phenol derivative in an inert organic solvent, at room, or nearly room, temperatures.

Examples of organic acids suitable for the intended purpose are selected from the aprotic solvents, such as, e.g., ethyl acetate or aliphatic chlorinated hydrocarbons.

The so obtained solution is then cooled to a temperature of approximately 0° C., and to it a condensation agent is added, with a condensation agent/aminoacid molar ratio equal to, or approximately equal to, 1.

The condensation agent typically used is dicyclohexyl-carbodiimide (DCI).

The (a) Step

In the (a) step of the process of the present invention, the reaction of esterification between the symmetrical anhydride of the α-amino-protected Ala aminoacid and the connection hook of the resin is carried out in an inert organic solvent, in the presence of catalysts.

Organic solvents suitable for the intended purpose are selected from aliphatic chlorocarbons, aliphatic ketones or alkyl esters.

Specific examples for said solvents are N,N-dimethylformamide (DMF), chloroform, ethyl acetate, tetrahydrofuran.

The catalysts are selected from those known from the prior art.

In particular, 4-dimethylaminopyridine and N-methylmorpholine are used.

The temperatures at which the esterification reaction is carried out can generally range from $-10°$ C. to $40°$ C., and the corresponding times are the required times for completing, or substantially completing, the reaction.

The (b) Step

At the end of the esterification reaction, in the (b) step the protecting group is removed from the α-amino group.

In particular, when the protecting group is fluorenyl-methyl-oxy-carbonyl (Fmoc), such removal is carried out by treating the peptide-resin with a (20:80, v/v) piperidine/DMF mixture for a total time of approximately 10 minutes.

The (c) and (e) Steps

After the removal of the α-amino-protecting group, and suitable washing of peptide-resin product, in the (c) and (e) steps of the present invention the successive aminoacids are condensed by means of the acylation reaction between the aminoacids, suitably protected and pre-activated in correspondence of their carboxy group, and the de-protected amino group of the aminoacid bonded to the resin.

In particular, the acylating reaction is carried out in an inert organic solvent, in the presence of catalysts.

The inert organic solvents are selected from aliphatic chlorinated hydrocarbons, aliphatic ketones or alkyl esters.

Preferably, N,N-dimethylformamide (DMF), chloroform, ethyl acetate, tetrahydrofuran are used.

The catalysts are selected from those known from the art.

In particular, for the Asn radical, 1-hydroxybenzotriazole (HOBT) is used.

The temperatures at which the acylation reaction is carried out are generally comprised within the range of from $-10°$ to $40°$ C.

The reaction is preferably carried out at room, or nearly room, temperatures, and the corresponding times are those necessary for completing, or substantially completing, the reaction.

The (f) Step

The removal of polypeptide (I) from the insoluble solid support can be carried out according to known general techniques by acidic or basic hydrolysis, aminolysis or alcoholysis.

The reaction is typically carried out by suspending the peptide-resin in a (90:10, v/v) trifluoroacetic acid/water solution, at a temperature comprised within the range of from $10°$ to $30°$ C.

At the end of the reaction, the resin is filtered off from the reaction mixture, is repeatedly washed with water and is filtered again.

The combined filtrates are concentrated to dryness by evaporation, are dissolved in water and are freeze-dried.

The (g) Step

The raw polypeptide (I) obtained from the (f) step is then purified by means of the sequence of steps of gel-filtration chromatography and ion-exchange chromatography.

The fractions corresponding to the desired product are collected and freeze-dried.

At the end of the process of the present invention, an overall chromatographic yield of 59%, and a yield of purified fraction of 73%, relatively to the polypeptide released from the resin, is obtained.

Polypeptides having the general formula (I) are endowed with a good immunogenic activity.

The peptides wherein n ranges from 3 to 40 are particularly suitable for the purposes of the present invention.

In fact, it was found that when said polypeptides, in a complete and/or incomplete Freund coadjuvant, are injected to strains of mice which had resulted to be nonresponder for (Asn-Ala-Asn-Pro)$_{40}$ polypeptide, induced the formation of antipolypeptide antibodies.

Therefore, said polypeptides can be used for the preparation of antimalarial vaccines efficacious in all patients.

Furthermore, said polypeptides can be used for the preparation of diagnostic kits, and in detecting systems for antisporozoite antibodies in samples of blood from malariated persons.

The following experimental examples are illustrative and not limitative of the invention.

EXAMPLE 1

Synthesis of
(Asn-Val-Asp-Pro-Asn-Ala-Asn-Pro)$_3$-(Asn-Ala-Asn-Pro)$_3$-Asn-Ala The synthesis was carried out on an automatic Beckman synthetizer model 990 B, using a commerical polyacrylamidic resin (Cambridge Research Biochemicals. Pepsyn A) functionalized with norleucine, as the internal reference aminoacid, and p-hydroxy-methyl-phenoxy-acetic acid as the "reversible peptide-resin connection hook".

One gram of resin was swollen for 16 hours in 32 ml of N,N-dimethylformamide (DMF) at room temperature ($20°$-$25°$ C.), with stirring.

After washing the resin with DMF (10 times, 1 minute each time), the first aminoacidic radical (Ala) was incorporated by means of the reaction of esterification, on the reversible hook, of the symmetrical anhydride of Ala, protected on its α-amino group with fluorenyl-methyl-oxy-carbonyl (Fmoc) protecting group.

2.17 g (1.8 mmol) of (Fmoc-Ala)$_2$O, 0.2000 ml (1.8 mmol) of N-methylmorpholine (NMM), and 0.022 g (0.18 mmol) of 4-dimethylaminopyridine (DMAP) were added in this order, and dissolved in 16 ml of DMF. The reaction mixture was maintained at room temperature for approximately 30 minutes.

At the end of the reaction of esterification, the resin was repeatedly washed according to the following washing cycle:

5 washes with DMF, of 1 minute each;
1 wash with a (20:80, v/v) piperidine/DMF solution, for 3 minutes;

1 wash with a (20:80, v/v) piperidine/DMF solution, for 7 minutes;
10 washes with DMF, of 1 minute each;
5 washes with DMF, of 1 minute each.

Then, the other aminoacids were all incorporated, one at a time, according to the desired sequence, by means of the reaction of acylation between the Fmoc-α-amino protected, activated-carboxy aminoacidic radical, and the growing polypeptidic chain.

The acylation reaction was carried out at room temperature for 50 minutes, by using the symmetrical anhydrides of Fmoc-aminoacids Ala, Val, Asp and Pro (1.8 mmol of the symmetrical anhydride in 16 ml of DMF) and the pentafluorophenyl-ester of Fmoc-Asn (1.8 mmol of Fmoc-Asn OPFP in 16 ml of DMF in the presence of 0.244 g (1.8 mmol) of 1-hydroxy-benzotriazole (HOBT).

The symmetrical anhydride of the protected aminoacids was prepared, immediately before the acylation reaction, by reacting 3.6 mmol of Fmoc-aminoacid with 0.371 g (1.8 mmol) of di-cyclohexyl-carbo-diimide (DCI) in 20 ml of $CH_2Cl_2$, at room temperature for 10 minutes. At the end of the reaction, the formed dicyclohexyl-urea was filtered off, the solvent was evaporated and the so-obtained symmetrical anhydride was recovered.

For each acylation reaction, the completion of the formation of the amidic bond was verified by means of the ninhydrin test (E. Kaiser et al., Anal. Biochem., 1980 34, 595), and the tri-nitro-benzene-sulphonic acid test (W. S. Hancock et al., Anal. Biochem., 1976 71, 261).

Said tests gave negative results after 30 minutes of reaction.

At the end of the assemblage of the desired sequence, the aminoacidic analysis of the peptide-resin was performed, and the following results were obtained (the theoretical values are in brackets):

| Asx | Pro | Ala | Val | Nle |
|---|---|---|---|---|
| 18.64 (19) | 9.75 (9) | 7.00 (7) | 3.12 (3) | 1.28 |

By Asx: either Asn or Asp is meant.

The so-synthetized polypeptide was then removed from the resin by means of the reaction with 50 ml of (90:10 v/v) trifluoroacetic acid/water solution at a temperature of 20° C. for 3 hours.

The resin was subsequenntly separated from the reaction mixture by filtration under vacuum, then it was washed 3 times, each time with 20 ml of water, and was finally filtered.

The filtrates were combined and were concentrated to dryness by evaporation, they were then dissolved in water and freeze-dried.

The yield of polypeptide release resulted to be higher than 98%, on the basis of the analysis of the residual resin.

The so-obtained polypeptide was purified by gelfiltration chromatography, over a column of 85×2.6 cm of Sephadex G-25 resin, eluted with 0.1 M $CH_3COOH$, at the flow rate of 38 ml/hour.

The fractions corresponding to the main peak were collected and freeze-dried.

The polypeptide was furthermore purified by ionexchange chromatography, over Whatmann DE-52 resin (column of 25×2.6 cm, eluted with a linear gradient of 0.1–0.5 M $NH_4HCO_3$, at a flow rate of 36 ml/hour).

The fractions corresponding to the main peak were collected and freeze-dried.

The aminoacidic analysis of the purified polypeptide resulted to be the following:

| Asx | Pro | Ala | Val |
|---|---|---|---|
| 18.66 (19) | 9.48 (9) | 7.00 (7) | 3.02 (3) |

The total chromatographic yield, based on the end contents of the resin and on the release yield, resulted of 59%. The yield of purified product resulted of 73%.

We claim:

1. Immunologically active polypeptides of the following general formula:

(Asn-Val-Asp-Pro-Asn-Ala-Asn-Pro)$_3$-(Asn-Ala-Asn-Pro)$_n$-Asn-Ala wherein:
Ala=alanine
Asn=asparagine
Asp=aspartic acid
Pro=proline
Val=valine
and wherein n has a value within the range of from 3 to 40.

2. Polypeptides according to claim 1, wherein n has a value of 3.

* * * * *